United States Patent [19]

Witton

[11] 4,206,752

[45] Jun. 10, 1980

[54] SUPPORT DEVICE

[76] Inventor: Norman N. Witton, Bank House, Shard La., Blackpool, England

[21] Appl. No.: 943,337

[22] Filed: Sep. 18, 1978

[30] Foreign Application Priority Data

Sep. 17, 1977 [GB] United Kingdom .............. 38868/77

[51] Int. Cl.² ............................................. A61F 5/00
[52] U.S. Cl. ................................................. 128/79
[58] Field of Search ................................. 128/79, 94

[56] References Cited

U.S. PATENT DOCUMENTS

| 2,264,934 | 12/1941 | Cronk | 128/79 |
| 2,868,192 | 1/1959 | Dannen | 128/79 |
| 3,926,184 | 12/1975 | Gehl | 128/79 |

FOREIGN PATENT DOCUMENTS

| 491522 | 2/1930 | Fed. Rep. of Germany | 128/79 |
| 714925 | 12/1941 | Fed. Rep. of Germany | 128/79 |

Primary Examiner—Lawrence W. Trapp
Attorney, Agent, or Firm—Shoemaker and Mattare, Ltd.

[57] ABSTRACT

A sex-aid of medical application which comprises a support element intended for location adjacent and in contact with an erect or partially erect penis so as to maintain the same in an upwardly directed disposition, and a belt or the like engageable with the support element and intended to extend about the wearer's body for linking the support element thereto.

A method of producing such a sex-aid is also disclosed.

6 Claims, 19 Drawing Figures

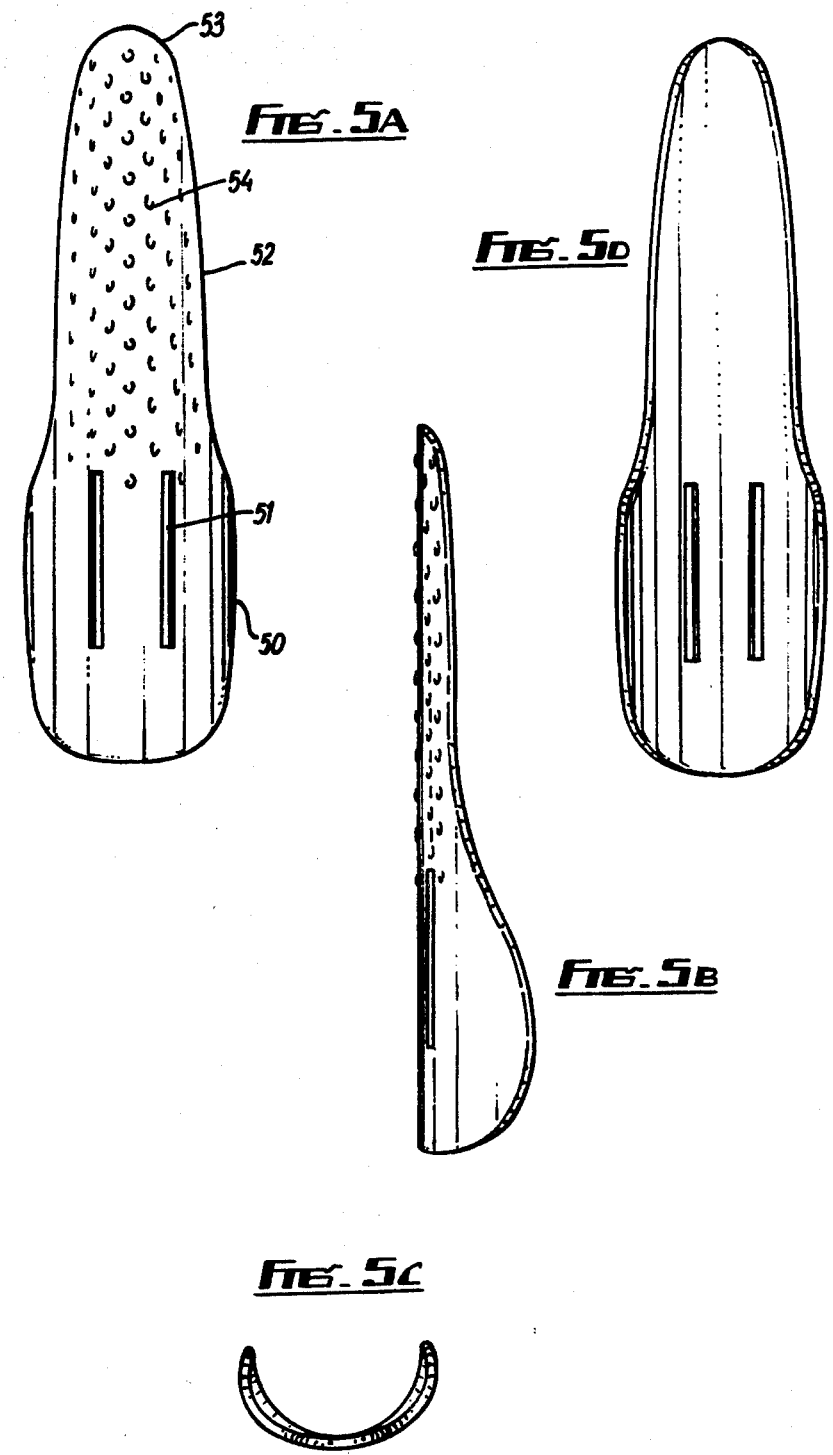

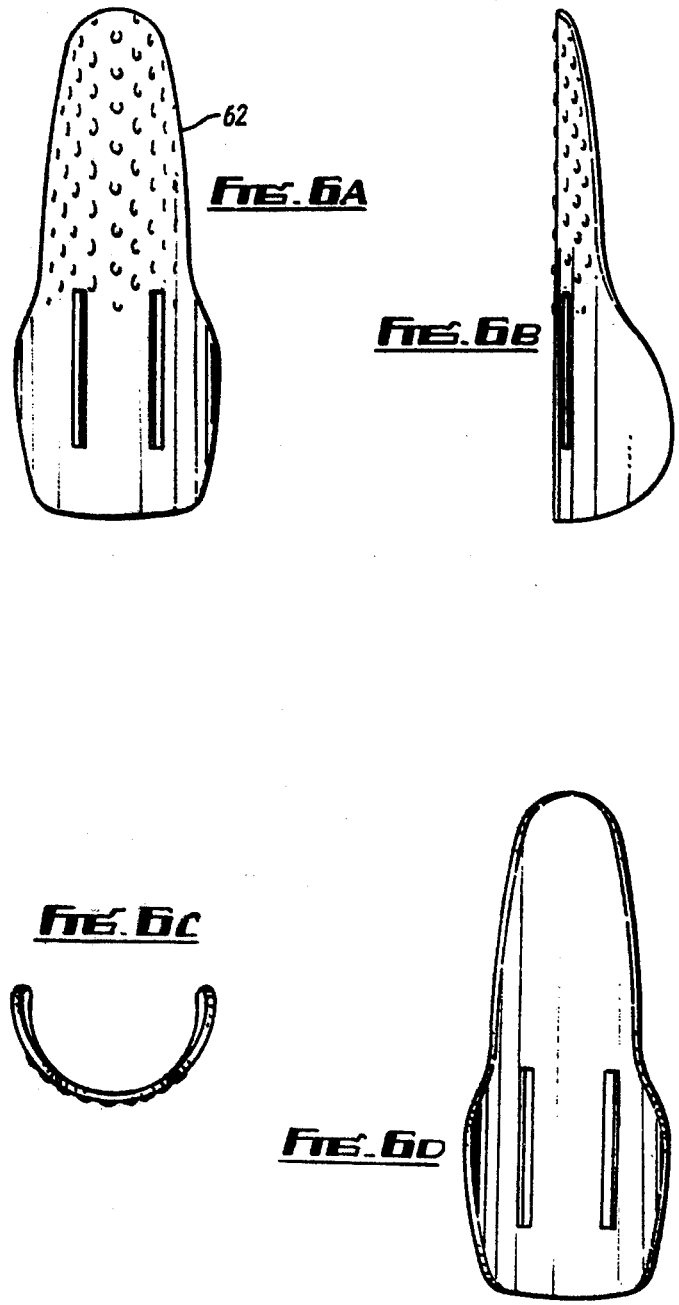

SUPPORT DEVICE

This invention relates to a sex-aid in the form of a device for use in supporting the penis during sexual intercourse, and a method for the production of such a sex-aid.

An object of the invention is to provide a sex-aid of assistance in the case where difficulty is encountered in achieving or maintaining an adequate erection in terms of stiffness and/or upward inclination of the penis.

According to the invention therefore there is provided a sex-aid in the form of a support device comprising a support element adapted to fit alongside the penis with the penis directed upwardly, and connection means arranged for linking the support element to the user's body whereby in use the penis is supported against movement away from the said upwardly directed disposition of same.

With this arrangement it will be appreciated that, in the case where only a partial erection can be achieved or maintained, the device can afford assistance in so far as it can help maintain the upward direction of the penis and possibly also may supplement the stiffness of same due to the reinforcing action of the support element.

With regard to the nature of the support element this may take any suitable form but preferably comprises a thinwalled structure appropriately formed so as to fit snugly in position and not to cause discomfort in use. Thus, the support element may comprise a shaped plastics or rubber shell having a soft and/or smooth surface and no exposed sharp or rough edges. In order to impart stiffness, said shell may be relatively stiff, such stiffness being a consequence of the properties of the material from which the shell is formed and/or due to a stiffening insert or inserts in the shell.

With regard to the connection means, this also may take any suitable form but preferably comprises a belt or tie attached to the support element and arranged to be fastened around the waist or lower portion of the user. Most conveniently a rubber belt or strap having a buckle or other adjustable fastener is used. Alternatively or additionally, adhesive fasteners of the kind conventionally used in contact with the skin may be used.

The invention also includes a method of producing a sex-aid as aforesaid.

The invention will now be described further by way of example only and with reference to the accompanying drawings in which.

Figure 1:
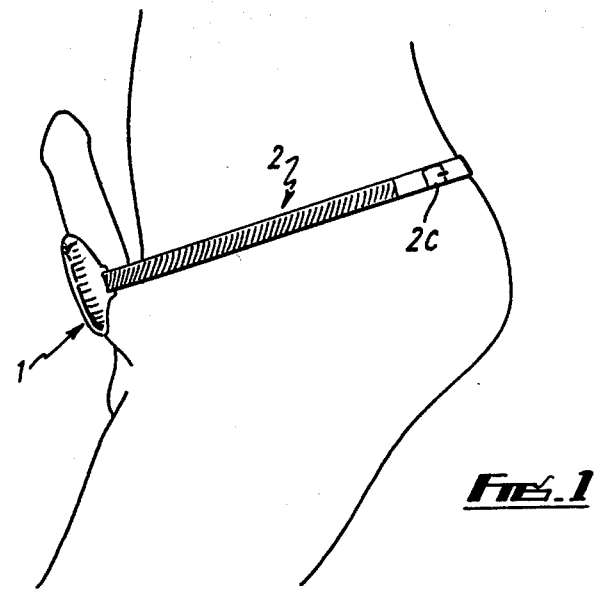
FIG. 1 is a diagrammatic view showing the sex-aid of the invention in use.
Figure 2:
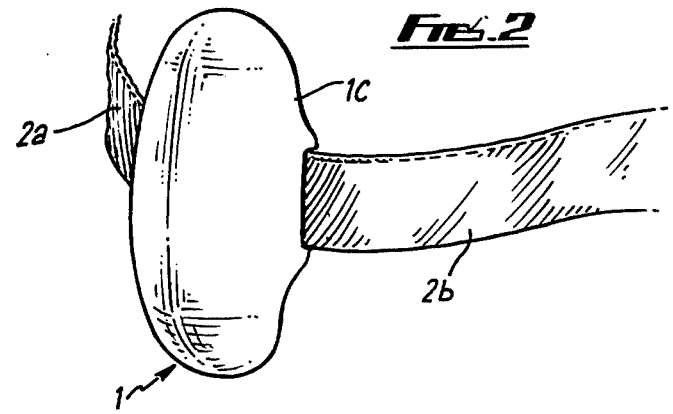
FIG. 2 is a diagrammatic perspective view of the aid to a larger scale.
Figure 3:
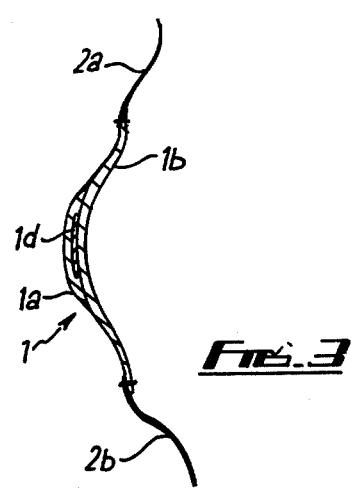
FIG. 3 is a sectional view of the aid.
Figure 4A:
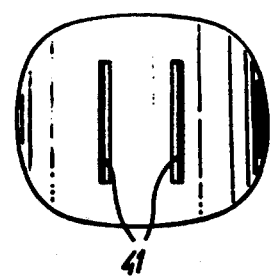
Figure 4B:
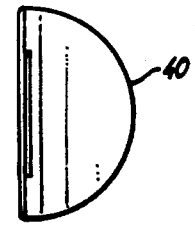
Figure 4C:
Figure 4D:
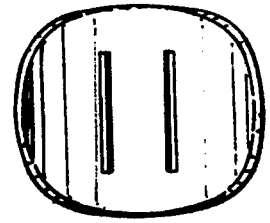
Figure 7:
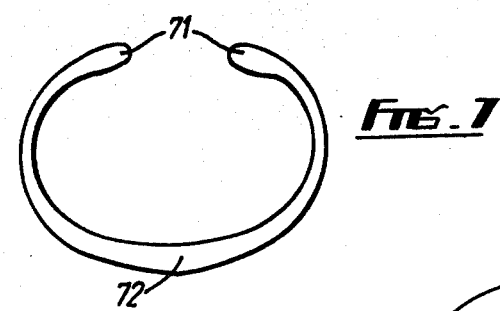
Figure 8:
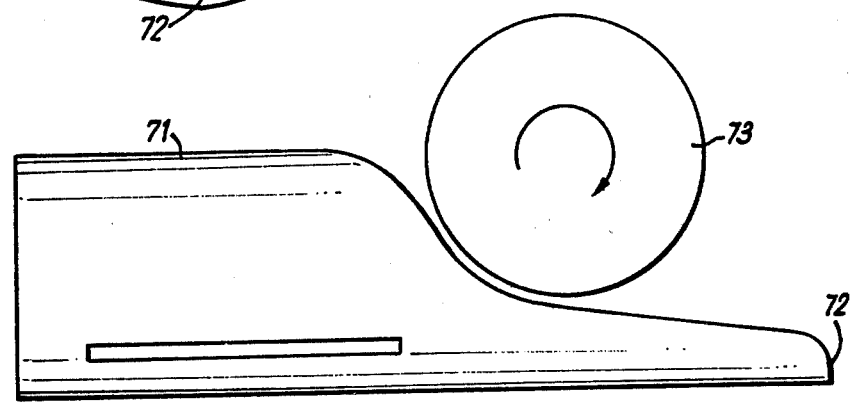
Figure 9:
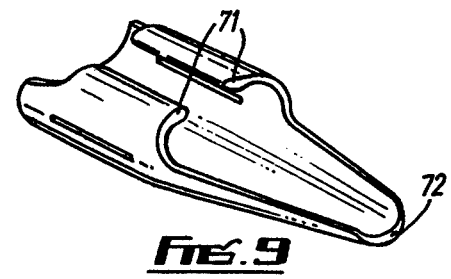
Figure 10:
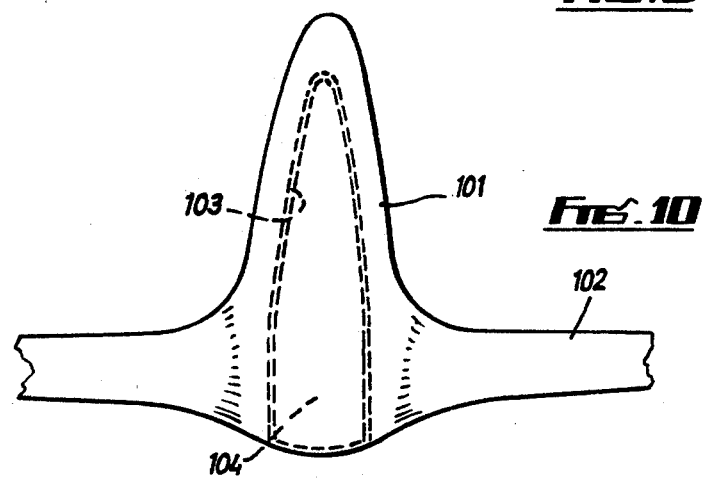

FIGS 4A to D are front, side, plan and rear elevations respectively of an alternative form of support element to that shown in FIGS. 1 to 3;

FIGS. 5A to D are views corresponding to FIGS. 4A to D and show a modified form of the support elements shown in such latter figures;

FIGS. 6A to D show a still further modified form of support element in front, side, plan and rear elevations respectively;

FIG. 7 is an end elevation of an extruded starting material for use in producing the sex-aid as shown in FIGS. 5A to 5D;

FIG. 8 is a diagrammatic side elevation of a length of the material as shown in FIG. 7 at an intermediate stage in the machining of such material to produce the finished sex-aid;

FIG. 9 is a perspective view, drawn to a smaller scale, of a finished sex-aid, as produced from the starting material illustrated in FIG. 7; and FIG. 10 is a diagrammatic plan view of a sex-aid of the kind shown in FIG. 2.

The sex-aid shown in FIGS. 1 to 3 of the drawings is in the form of a support device comprising a support element 1 and a belt 2.

The support element 1 comprises a thin-walled moulded rubber shell of elongated form which has a smooth convex outer surface 1a, a smooth concave inner surface 1b, and a smoothly curved peripheral edge 1c. The rubber material used for the shell is of a relatively self-supporting yet soft nature and may be natural or synthetic. A relatively rigid plastics insert 1d in the form of a rod or strip is moulded in the shell so that it extends longitudinally thereof and is wholly enclosed by the rubber material.

The belt 2 comprises two thin, flexible rubber strips 2a, 2b which are fastened at ends thereof to opposite sides of the support element 1 and which can be detachably and adjustably interconnected at the other ends by means of a buckle 2c or the like.

In use, the concave inner surface 1b of the shell is applied to the outer surface of the user's penis with the penis directed upwardly and the belt 2 is fastened around the user's waist.

The shell is shaped to fit snugly and comfortably against the penis whilst extending longitudinally thereof, and the shell is held securely in position by means of the belt 2.

With this arrangement, the penis is held upwardly directed even if a full erection thereto cannot be achieved or maintained, and stiffness is supplemented by the longitudinal stiffness of the shell as derived from or supplemented by the insert 1d.

Undue discomfort can be avoided due to the soft, smooth nature of the shell and the absence of sharp or rough edges thereto.

As an alternative to the reinforced shell as shown in FIS. 1 to 3, the support element may comprise a relatively rigid support member of generally part-cylindrical form and having slots therein whereby the same is attached to the belt.

One form of support member is shown in FIGS. 4A to D, and will be seen to comprise a part-cylindrical shell 40, the ends of such shell, when viewed in side elevation, being of semi-circular form, there being slots 41 in the shell in spaced apart disposition and arranged parallel to the shell axis to receive the belt into engagement therewith. The support member is moulded from a soft synthetics plastics material, and the edges and corners thereof are radiussed or rounded to avoid discomfort in use.

In a modified form of support member, see now FIGS. 5A to D, the part-cylindrical shell 50 with slots 51 includes an axially directed extension 52 of a length approximately equal to the axial extent of the said shell, the extension being of approximately rectangular shape when viewed in front elevation and being of like thickness to the wall thickness of the shell. The extension is positioned symmetrically in relation to the part-cylindrical shell, and is of arcuate form when viewed in transverse cross-section in conformity with the curvature of the corresponding parts of the shell. The remote end 53 of the extension is curved thus to avoid the presence of sharp corners, whilst at its outer surface and centrally thereof the extension is formed with a dimpled or roughened surface 54, to enhance sexual sensations during intercourse.

A further modified form of support member is shown in FIGS. 6A to D, such member differing from that of FIGS. 5A to D only as regards the axial extent of the extension 62.

The support members of FIGS. 4A to D, 5A to D, and 6A to D will be selected according to the degree of support required, the support available clearly being greater with the member of FIGS. 5A to D than with FIGS. 4A to D, and still greater with the member of FIGS. 6A to D.

A sex-aid of those kinds shown in FIGS. 4 to 6 can conveniently be manufactured from extruded material of a suitable transverse cross-section, such extruded material subsequently being cut to length and machined to assume a requisite final form.

A suitable starting material may have the cross-section as shown in FIG. 7, the longitudinal edges being thickened, as at 71, to provide for an adequate rigidity at such edges whilst permitting of a relative displacement thereof to vary the dimensions of the aid. A further thickened region 72 exists along the line of symmetry of the article, again to impart rigidity to the aid.

The preferred material of choice is a non-toxic synthetic plastics material, and the shaping of the aid is affected by machining of the two ends, as represented by the cutter 73 shown in FIG. 8, the left hand end of the aid (as seen in the drawing) being shown in its original form and requiring to be shaped in analogous manner to the shaping evident at the right hand end.

The finished product is shown in FIG. 9, the thickened edges 71 and thickened central region 72 being readily apparent therein.

The aid as shown in FIG. 2 can conveniently be made by a moulding process, the shell 101 and belt 102 (see FIG. 10) being moulded as an integral structure and the former having a cavity 103 therein to receive a reinforcing element 104, if necessary.

It is of course to be understood that the invention is not intended to be restricted to the details of the above embodiments which are described by way of example only. Thus, for example, as an alternative to producing the aid by way of a moulding process and/or by machining of a suitable starting element, the aid may be fabricated as a lamination of a plurality of individual plies each selected for its physical characteristics.

What I claim is:

1. A support device comprising a support element adapted to fit alongside the penis with the penis directed upwardly, an arcuate part-cylindrical shell, said shell having a plurality of axially directed slots defined therein, an axially directed extension of arcuate transverse and rectangular longitudinal section on said shell, said extension having a length which is approximately equal to the axial extent of said shell, said extension having a roughened external surface, and connection means received in said slots for linking the support element to the user's body whereby in use the penis is supported against movement away from the said upwardly directed disposition of same.

2. A support device as claimed in claim 1 having a stiffening insert.

3. A support device as claimed in claim 1 in which the connection means is a belt passing through slots in the support elements.

4. A support device as claimed in claim 1 in which the support element is a moulded shell of elongate form having a smooth convex outer surface, a smooth concave inner surface and a smoothly curved peripheral edge.

5. The method of producing a support device as claimed in claim 1, which device comprises a belt and a moulded shell, wherein the belt and shell are moulded integrally.

6. The method as claimed in claim 5, wherein a cavity is formed in the shell to receive a stiffening member into engagement therewith.